United States Patent
Poigny et al.

(10) Patent No.: US 8,906,416 B2
(45) Date of Patent: Dec. 9, 2014

(54) XANTHENEDIONE DERIVATIVES FOR THE TREATMENT OF PIGMENTATION AND SKIN AGEING DISORDERS

(75) Inventors: Stéphane Poigny, Saubens (FR); Françoise Belaubre, Villeneuve Tolosane (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 13/808,456

(22) PCT Filed: Jul. 8, 2011

(86) PCT No.: PCT/EP2011/061637
§ 371 (c)(1),
(2), (4) Date: Jan. 4, 2013

(87) PCT Pub. No.: WO2012/004390
PCT Pub. Date: Jan. 12, 2012

(65) Prior Publication Data
US 2013/0108568 A1    May 2, 2013

(30) Foreign Application Priority Data

Jul. 9, 2010  (FR) ..................................... 10 55595

(51) Int. Cl.
| | | |
|---|---|---|
| *C07D 311/82* | (2006.01) | |
| *A61K 8/49* | (2006.01) | |
| *C07D 309/10* | (2006.01) | |
| *C07D 407/12* | (2006.01) | |
| *A61K 8/60* | (2006.01) | |
| *A61K 8/69* | (2006.01) | |
| *A61Q 5/08* | (2006.01) | |
| *A61Q 19/02* | (2006.01) | |
| *A61Q 19/08* | (2006.01) | |
| *C07H 15/26* | (2006.01) | |

(52) U.S. Cl.
CPC .............. *C07D 311/82* (2013.01); *C07H 15/26* (2013.01); *A61K 8/498* (2013.01); *A61Q 5/08* (2013.01); *A61Q 19/02* (2013.01); *A61Q 19/08* (2013.01); *A61K 8/69* (2013.01); *A61K 8/60* (2013.01); *C07D 407/12* (2013.01); *C07D 309/10* (2013.01)
USPC ............... 424/489; 424/502; 424/60; 424/62; 424/70.6; 424/70.9; 514/454; 549/224

(58) Field of Classification Search
CPC .. C07D 309/10; C07D 311/82; C07D 407/12; C07H 15/26; A61K 8/60; A61K 8/69; A61K 8/498; A61Q 5/08; A61Q 19/02; A61Q 19/08
USPC ................... 424/489, 502, 60, 62, 70.6, 70.9; 514/454; 549/224

See application file for complete search history.

(56) References Cited

U.S. PATENT DOCUMENTS

2004/0047832 A1    3/2004  Pauly et al.

FOREIGN PATENT DOCUMENTS

| FR | 2756183 A1 | 5/1998 | |
|---|---|---|---|
| WO | WO 02/45728 A1 | 6/2002 | |
| WO | WO 2006/055688 A1 | 5/2006 | |
| WO | WO2006055688 A1 * | 5/2006 | ............. A61K 36/38 |

OTHER PUBLICATIONS

"Prevention", Merriam-Webster Online Dictionary [online], [retrieved Feb. 23, 2014] Retrieved from the Internet: <URL: http://www.merriam-webster.com/dictionary/prevention>.*
Kozlov et al., "Reaction of Long-Chain Vanillyl Esters with CH-Acids and 2-Naphthylamine", 2004, Chemistry of Natural Compounds, 40:79-82.*
Arezzini et al., "Synthesis, chemical and biological studies on new Fe3+-glycosilated β-diketo complexes for the treatment of iron deficiency," European Journal of Medicinal Chemistry, vol. 43, 2008, pp. 2549-2556.

(Continued)

*Primary Examiner* — Jane C Oswecki
(74) *Attorney, Agent, or Firm* — Birch, Stewart, Kolasch & Birch, LLP

(57) ABSTRACT

The invention relates to compound of generic formula (I) in which: $R_1$ and $R_2$ represent: OH, a hydrogen atom, a $C_1$-$C_6$ alkyl radical a $C_1$-$C_6$ alkoxy radical, a halogen, or $OCOR_3$; $R_3$ represents: a $C_1$-$C_{24}$ alkyl radical a $C_{12}$-$C_{24}$ alkenyl radical comprising at least one unsaturation; $R_4$ represents: $COR_5$, a glucide substituted or not by one or more acetyl radical(s); $R_5$ represents: a $C_{10}$-$C_{24}$ alkyl radical or a $C_{12}$-$C_{24}$ alkenyl radical comprising at least one unsaturation; $R_6$ and $R_7$ represent:—simultaneously a hydrogen atom or a methyl radical, or—when $R_6$ represents a hydrogen atom, $R_7$ represents a $C_1$-$C_6$ alkyl radical or a phenyl substituted or not by one or more $C_1$-$C_3$ alkoxy radical(s) or one or more halogen(s) or—$R_6$ and $R_7$ are bonded together and form a $C_3$-$C_6$ cycloalkyl, and pharmaceutically or cosmetically acceptable salts.

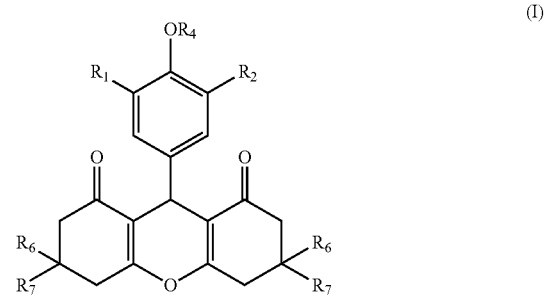

(I)

25 Claims, No Drawings

(56) References Cited

OTHER PUBLICATIONS

Bessou-Touya et al., "Chimeric human epidermal reconstructs to study the role of melanocytes and keratinocytes in pigmentation and photoprotection," The Journal of Investigative Dermatology, vol. 111, No. 6, Dec. 1998, pp. 1103-1108.

Chakravarti et al., "The reactivity of dimethyldihydroresorcin. Part 1. Condensation with aromatic aldehydes," Journal of Indian Institute of Science, Section A, vol. 14, Jan. 1, 1931, pp. 141-156, XP008134923.

Das et al., "An efficient synthesis of 1.8-dioxo-octahydroxanthenes using heterogeneous catalysts," Catalysis Communications, vol. 8, 2007, pp. 535-538.

He et al. "Glycerol as a promoting medium for electrophilic activation of aldehydes: catalyst-free synthesis of di(indolyl)methanes, xanthene-1,8(2H)-diones and 1-oxo-hexahydroxanthenes," Green Chem., vol. 11, 2009, XP008134934, pp. 1767-1773.

International Search Report (Forms PCT/ISA/220 and PCT/ISA/210) for International Application No. PCT/EP2011/061637, dated Sep. 1, 2011.

Kantevari et al., "TMSCl mediated highly efficient one-pot synthesis of octahydroquinazolinone and I,8-dioxo-octahydroxanthene derivatives," ARKIVOC, 2006, vol. XVI, pp. 136-148.

Kozlov et al., "Reaction of long-chain vanillyl esters with CH-Acids and 2-Naphthylamine," Chemistry of Natural Compounds, vol. 40, No. 1, 2004, XP-002630614, pp. 79-82.

Kozlov et al., "Vanilline alkanoates in the synthesis of hexahydrobenzacridine and octahydroxanthene derivatives," Russian Journal of General Chemistry, vol. 75, No. 4, 2005, XP-002630615, pp. 617-621.

Mohri et al., "Synthesis of glycosylcurcuminoids," Chem. Pharm. Bull. vol. 51, No. 11, 2003, pp. 1268-1272.

Redoules et al., "Characterisation and assay of five enzymatic activities in the stratum corneum using tape-strippings," Skin Pharmacol Appl Skin Physiol, vol. 12, 1999, pp. 182-192.

Scheider-Liebeler et al., "Synthesis of basically substituted 1,8-dioxooctahydroxanthenes. 3. Reaction of dialkylaminoethyl chlorides with condensation products of glyoxylic acid," Archiv. der Pharmazie, vol. 305, No. 7, 1972, XP-002631596, pp. 534-538.

Sonn et al., "Dihydroresorcinols," Journal Fuer Praktische Chemie (Leipzig), vol. 155, 1940, pp. 65-76.

Takagi et al., "β-Glucocerebrosidase activity in mammalian stratum corneum," Journal of Lipid Research, vol. 40, 1999, pp. 861-869.

Wen et al., "Synthesis and biological evaluation of helicid analogues as novel acetylcholinesterase inhibitors," European Journal of Medicinal Chemistry, vol. 43, 2008, pp. 166-173.

\* cited by examiner

XANTHENEDIONE DERIVATIVES FOR THE TREATMENT OF PIGMENTATION AND SKIN AGEING DISORDERS

The present invention relates to xanthenedione derivatives and pharmaceutical or cosmetic compositions that contain them, their method of preparation and their uses particularly as medicine or as cosmetic active ingredient.

The novel compounds according to the present invention come in the form of xanthenedione precursors. The use of these precursors enables a slow release of the xanthenedione functions in the cutaneous medium.

They may be on the one hand glycosides, which stem from the condensation of glucose and xanthenedione functions.

In this case, the principle of the invention is linked to the use of glucocerebrosidase, which is a lysosomal enzyme present in all cells and thus naturally present in the skin (Yutaka Takagi, Ernst Kriehuber, Genji Imokawa, Peter M. Elias, and Walter M. Holleran, β-Glucocerebrosidase activity in mammalian stratum corneum, *The Journal of Lipid Research*, Vol. 40, 861-869, (1999). Glucocerebrosidase hydrolyses the active precursor, thereby releasing the biologically active substance (see diagram 1), namely the xanthenedione function.

The enzymatic hydrolysis by glucocerebrosidase slowly releases the xanthenedione function. This slow release makes it possible to avoid the over concentration of the active ingredient. Thus, the slow release of the active ingredient ensures a better bioavailability thereof in the cutaneous medium and thus more efficient protection.

They may be on the other hand alkylic or alkenylic ester of xanthenediones. The esters are also easily cleavable by the esterases present in the skin (Redoules, D., Tarroux, R., Assalit, M. F. and Perié, J. J. Characterization and assay of five enzymatic activities in the stratum corneum using tape-stripping, *Skin Pharmacol. Appl. Skin Physiol.*, 12, 182-192 (1999)). The cleavage of the esters by the esterases present in the skin then enables a slow diffusion of the active ingredients (see diagram 1), which corresponds to the concept of "drug delivery".

Diagram 1: Cleavage of compounds of generic formula (I) by the esterases or glucocerebrosidase of the skin.

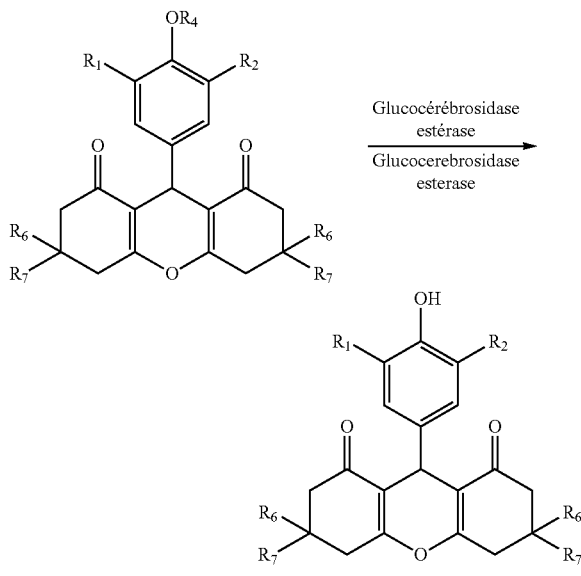

Thus, the object of the present invention is a compound of the following generic formula (I):

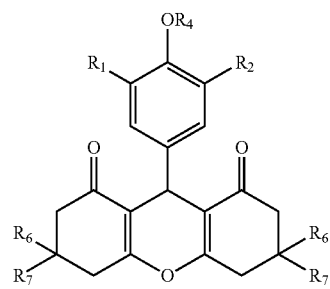

In which:
  $R_1$ and $R_2$ represent simultaneously or independently: OH, an atom of hydrogen, a $C_1$-$C_6$ alkyl radical, a $C_1$-$C_6$ alkoxy radical, a halogen, or $OCOR_3$;
  $R_3$ represents: a $C_1$-$C_{24}$ alkyl radical, a $C_{12}$-$C_{24}$ alkenyl radical comprising at least one unsaturation, advantageously from 1 to 6 and preferably from 1 to 4;
  $R_4$ represents: $COR_5$, a glucide radical substituted or not by one or more acetyl radical(s),
  $R_5$ represents: a $C_{10}$-$C_{24}$ alkyl radical, or a $C_{12}$-$C_{24}$ alkenyl radical comprising at least one unsaturation, advantageously from 1 to 6 and preferably from 1 to 4;
  $R_6$ and $R_7$ represent:
    simultaneously a hydrogen atom or a methyl radical, or when $R_6$ represents a hydrogen atom, $R_7$ represents a $C_1$-$C_6$ alkyl radical or a phenyl substituted or not by one or more $C_1$-$C_3$ alkoxy radical(s) or one or more halogen(s), or
    $R_6$ and $R_7$ are bonded to each other and form a $C_3$-$C_6$ cycloalkyl, and cosmetically and pharmaceutically acceptable salts.

Definitions:

"Alkyl radical" is taken to mean, according to the present invention, a saturated linear or branched aliphatic hydrocarbon chain and comprising the specified number of carbon atoms. Methyl, ethyl and propyl may for example be cited. The alkyl radical may in particular represent the hydrocarbon chain of a $C_1$-$C_{24}$ and in particular a $C_{10}$-$C_{24}$ saturated fatty acid.

The saturated fatty acids may be capric acid (10:0), undecylic acid (11:0), lauric acid (12:0), tridecylic acid (13:0), myristic acid (14:0), pentadecylic acid (15:0), palmitic acid (16:0), margaric acid (17:0), stearic acid (18:0), nonadecylic acid (19:0), arachidic acid (20:0), heneicosanoic acid (21:0), behenic acid (22:0), tricosanoic acid (23:0), lignoceric acid (24:0). In particular, the saturated fatty acids may be palmitic acid and stearic acid.

"Alkoxy radical" is taken to mean, according to the present invention, a linear or branched hydrocarbon chain comprising the number of carbon atoms indicated and an oxygen atom for example a methoxy radical, an ethoxy radical, a propoxy radical or a butoxy radical.

"Alkenyl radical" is taken to mean, according to the present invention, a linear or branched hydrocarbon chain comprising the number of carbon atoms indicated and comprising at least one unsaturation advantageously 1 to 6 and preferably 1 to 4. "Unsaturation" is taken to mean, according to the present invention, a C═C double bond.

The alkenyl radical may in particular represent a hydrocarbon chain stemming from a $C_{12}$-$C_{24}$ unsaturated fatty acid comprising at least one unsaturation, advantageously 1 to 6 and preferably 1 to 4.

The unsaturated fatty acids may be lauroleic acid (C12:1), myristoleic acid (C14:1), palmitoleic acid (C16:1), oleic acid (C18:1), ricinoleic acid (C18:1), gadoleic acid (C20:1), erucic acid (C22:1), α-linolenic acid (C18:3), stearidonic acid (C18:4), eicosatrienoic acid (C20:3), eicosatetraenoic acid (C20:4), eicosapentaenoic acid (C20:5), docosapentaenoic acid (C22:5), docosahexaenoic acid (C22:6), tetracosapentaenoic acid (C24:5), tetracosahexaenoic acid (C24:6), linoleic acid (C18:2), gamma-linolenic acid (C18:3), eicosadienoic acid (C20:2), dihomo-gamma-linolenic acid (C20:3), arachidonic acid (C20:4), docosatetraenoic acid (C22:2), docosapentaenoic acid (C22:5), adrenic acid (C22:4) and calendic acid (C18:3). In particular, the unsaturated fatty acids may be: α-linolenic acid (C18:3), oleic acid (C18:1), linoleic acid (C18:2), gamma-linolenic acid (C18:3) and dihomo-gamma-linolenic acid (C20:3).

"Acetyl" is taken to mean a salt or an ester of acetic acid.

Halogen is taken to mean an atom of chlorine, an atom of fluorine, an atom of bromine and an atom of iodine.

"Glucide" is taken to mean, according to the present invention, a class of organic molecules containing a carbonyl group (aldehyde or ketone) and several hydroxyl (—OH) groups.

The terms glucides, monosaccharides, saccharides, carbohydrates, sugars are equivalent in the present invention.

Advantageously, the glucide of the generic formula (I) is chosen from the monosaccharides.

More advantageously, the glucide of generic formula (I) is chosen from monosaccharides of the series D.

Even more advantageously, the glucide of generic formula (I) is chosen from the C3-C6 monosaccharides of series D, such as glyceraldehyde, erythrose, threose, ribose, arabinose, xylose, lyxose, allose, altrose, gulose, idose, talose, glucose, galactose, mannose, fructose and derivatives thereof such as their cyclic forms when they exist, of pyrannose or furanose type for example. The preferred monosaccharide in the present invention is D-glucopyrannose. The glucide may be bonded to the xanthenedione derivative by an α or β osidic type bond if the bond is on the anomeric carbon of the glucide. The glucide may also be bonded to the xanthenedione derivative by a simple ether bond if the bond is formed on the oxygen of a non-anomeric carbon of the glucide.

According to an embodiment of the invention, the compounds of generic formula (I) are those for which $R_1$ and $R_2$ represent simultaneously or independently a hydrogen atom or a $C_1$-$C_6$ alkoxy radical.

According to the invention, the compounds of generic formula (I) are those for which $R_4$ represents $COR_5$.

The invention also relates to compounds of generic formula (I) for which $R_5$ represents a $C_{14}$-$C_{18}$ alkyl radical or a $C_{14}$-$C_{18}$ alkenyl radical comprising from 1 to 3 unsaturations.

According to an embodiment of the invention, the compounds of generic formula (I) are those for which $R_4$ represents a glucide substituted or not by one or more acetyl radical(s), in particular a pyranose radical, if appropriate partially or totally acetylated.

According to the invention, the compounds of generic formula (I) are those for which $R_6$ and $R_7$ represent simultaneously a methyl radical.

The compounds of generic formula (I) may be chosen from the following list of compounds:
- 2-methoxy-4-(3,3,6,6-tetramethyl-1,8-dioxo-2,3,4,5,6,7,8,9-octahydro-1H-xanthen-9-yl)phenyl palmitate
- (9Z,12Z)-2-methoxy-4-(3,3,6,6-tetramethyl-1,8-dioxo-2,3,4,5,6,7,8,9-octahydro-1H-xanthen-9-yl)phenyl octadeca-9,12-dienoate
- (3R,4S,5S)-2-(acetoxymethyl)-6-(2-methoxy-4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate
- 9-(3-methoxy-4-((3S,4S,5S)-3,4,5-trihydroxy-6-(hydroxymethyl)tetrahydro-2H-pyran-2-yloxy)phenyl)-3,3,6,6-tetramethyl-3,4,5,6,7,9-hexahydro-1H-xanthene-1,8(2H)-dione
- (3S,4S,5S,6S)-2-(acetoxymethyl)-6-(2-methoxy-4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate
- 9-(3-methoxy-4-((2S,3S,4S,5R)-3,4,5-trihydroxy-6-(hydroxymethyl)tetrahydro-2H-pyran-2-yloxy)phenyl)-3,3,6,6-tetramethyl-3,4,5,6,7,9-hexahydro-1H-xanthene-1,8(2H)-dione
- (3R,4S,5S,6S)-2-(acetoxymethyl)-6-(4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate
- 3,3,6,6-tetramethyl-9-(4-((2S,3S,4S,5S)-3,4,5-trihydroxy-6-(hydroxymethyl)tetrahydro-2H-pyran-2-yloxy)phenyl)-3,4,5,6,7,9-hexahydro-1H-xanthene-1,8(2H)-dione.

The present invention also extends to the compound of generic formula (I'):

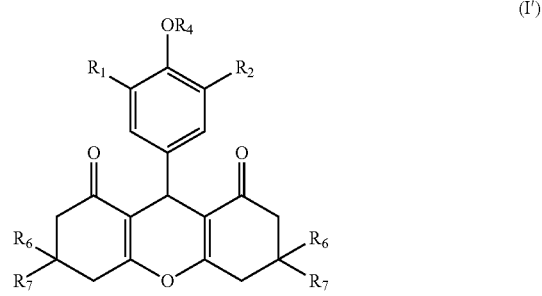

in which the radicals $R_1$, $R_2$, $R_3$, $R_4$, $R_5$, $R_6$ and $R_7$ have significations identical to those given previously, but in which $R_4$ may in addition represent a hydrogen atom or an acetyl radical, and pharmaceutically or cosmetically acceptable salts, for its use as medicine or as cosmetic active ingredient.

The invention also relates to the compounds of generic formula (I') defined above for their use in the depigmentation of the skin and/or head hair and/or body hair, in the treatment and/or in the prevention of the ageing of the skin or in the treatment and/or the prevention of the inflammation of the skin.

The invention also relates to the compounds of generic formula (I') defined above in which $R_4$ represents a hydrogen atom in the depigmentation of the skin and/or head hair and/or body hair, in the treatment and/or in the prevention of the ageing of the skin or in the treatment and/or the prevention of the inflammation of the skin.

The present invention relates to compounds of generic formula (I') for their use as active depigmenting ingredient, active anti-oxidant ingredient or active anti-inflammatory ingredient.

The depigmenting activity, which consists in a general manner in reducing and/or inhibiting the production of melanins responsible for pigmentation, or in reducing the transport of melanins in dendrites, may manifest itself through different types of actions according to the present invention:

reducing and/or eliminating pigment spots such as hyperpigmentation spots due to pro-inflammatory stress (brownish UV induced pigment spots, for example) and chloasmas, or instead;

bleaching and/or lightening the skin and/or body hair and/or head hair, preferentially in order to:

unify the complexion; which is characterised by obtaining a uniform, lighter, more transparent, more radiant skin complexion. The lustre of the complexion is thus improved. The advantages obtained are particularly interesting for sensitive skins whatever their nature (dry, normal, greasy) and more particularly dull and lustreless sensitive skins, and/or;

treat certain unsightly pigment spots due to an epidermal hyperpigmentation, especially such as ageing spots of the skin. The depigmenting activity according to the present invention then entails the visible reduction of the intensity and the size of the pigment spots and/or preventing the appearance of additional spots.

The present invention relates to compounds of generic formula (I') in which $R_4$ represents a hydrogen atom for their use as depigmenting active ingredient, antioxidant active ingredient or anti-inflammatory active ingredient.

The present invention also relates to the use of cosmetic compositions comprising a compound of generic formula (I') for depigmentation of the skin and/or head hair and/or body hair, the treatment and/or the prevention of the ageing of the skin or the treatment and/or the prevention of the inflammation of the skin.

The present invention relates to a method of bleaching and/or lightening of human skin and/or body hair and/or head hair comprising the application on the skin and/or body hair and/or head hair of a cosmetic composition containing at least one compound of generic formula (I').

The present invention relates to a cosmetic method of treatment and/or prevention of the ageing of the skin comprising the application on the skin of a cosmetic composition containing at least one compound of generic formula (I').

The present invention relates to a cosmetic method of treatment and/or prevention of inflammatory reactions of the skin comprising the application on the skin of a cosmetic composition containing at least one compound of generic formula (I').

The invention also extends to the method of synthesising compounds of generic formula (I), characterised in that two molecules of 1,3-diketone are made to react with an aldehyde in the presence of an acid or basic catalysis:

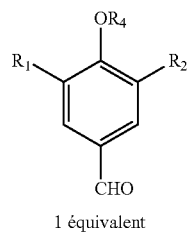

Aldehyde     1,3-diketone 1 equivalent

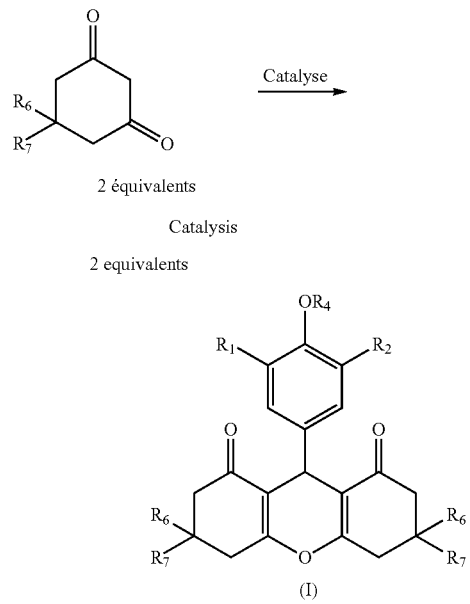

2 équivalents

Catalysis 2 equivalents with $R_1$, $R_2$, $R_3$, $R_4$, $R_5$, $R_6$ and $R_7$ having the same significations as those given in the generic formula (I).

For the synthesis of products of generic formula (I) with $R_4$=$COR_5$, a phenol is made to react with a $R_5COCl$ activated carboxylic acid

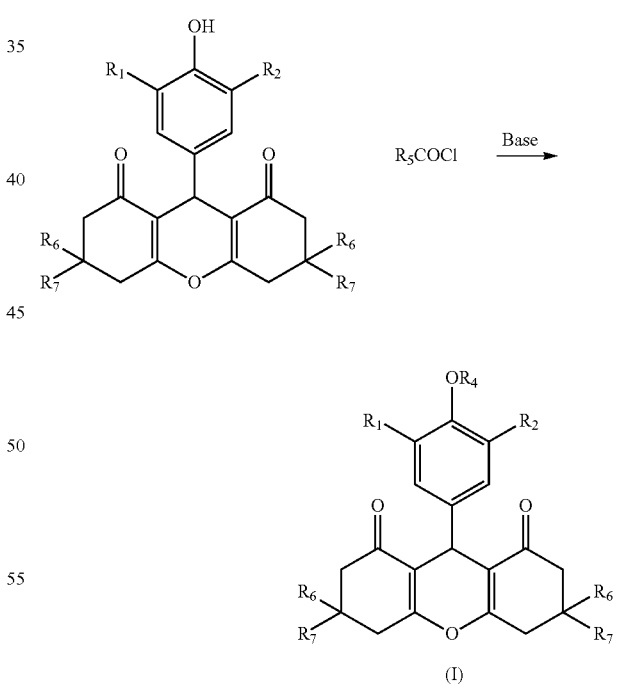

with $R_1$, $R_2$, $R_3$, $R_5$, $R_6$ and $R_7$ having the same significations as those given in the generic formula (I).

For the synthesis of products of generic formula (I) with $R_4$=a glucide substituted by one or more acetyl radical(s), a phenol is made to react with a glucide radical substituted by one or more acetyl radical(s).

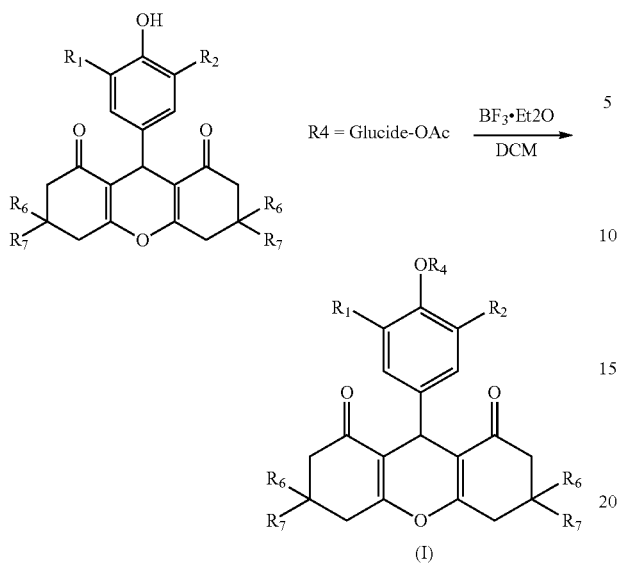

with $R_1$, $R_2$, $R_3$, $R_5$, $R_6$ and $R_7$ having the same significations as those given in the generic formula (I), which may be followed if appropriate by a saponification step.

1) General Protocol for Synthesising Compounds According to the Invention

EXAMPLE 1

-9-(4-hydroxy-3-methoxyphenyl)-3,3,6,6-tetramethyl-3,4,5,6,7,9-hexahydro-1H-xanthene-1,8(2H)-dione

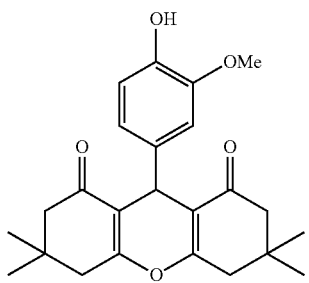

General Procedure A

The synthesis of the xanthenedione function is described in the literature in one or two steps from 1,3-diketone and an aldehyde in the presence of an acid or base catalysis (S. Kantevari et al., Arkivoc 2006, 136-148) (B. Das et al., Catalysis Communications 8 (2007) 535-538).

To a suspension of 1.40 g of 5,5-dimethyl-1,3-cyclohexanedione (dimedone, 10 mmol) and 0.76 g of vanillin (5 mmol) in 10 mL of acetonitrile, 0.63 mL of trimethylsilane chloride (5 mmol) are added. The mixture is taken to reflux to a temperature of 110° C. and the solubilisation of the particles in suspension into a clear, yellow solution is observed. After 6 h of reaction, the solution is cooled to ambient temperature for 10 minutes then is placed for 10 minutes in an ice bath. Water is then added in order to precipitate the xanthenedione obtained. The mixture is then filtered on a sinter with distilled water, then with n-pentane. The solid is dried in the vacuum oven for at least one night under 50 mbar and at 40° C. in order to obtain a white solid with a yield of 79%.

$^1$H NMR (400 MHz, CDCl$_3$): δ: 1.00 (s, 6H); 1.10 (s, 6H); 2.20 (dd, 4H); 2.45 (s, 4H); 3.87 (s, 3H); 4.66 (s, 1H); 5.60 (s, 1H); 6.58 (dd, 1H); 6.72 (d, 1H); 6.99 (d, 1H).

$^{13}$C NMR 100 MHz, CDCl$_3$): δ: 27.2; 29.2; 31.2; 32.1; 40.8; 50.7; 55.8; 112.2; 113.9; 115.7; 145.8; 162.0; 196.5.

MS (ESI+): 397.1 [M+H]$^+$

Rf (heptane/EtOAc; 1/1): 0.57

EXAMPLE 2

-9-(3,4-dihydroxyphenyl)-3,3,6,6-tetramethyl-3,4,5,6,7,9-hexahydro-1H-xanthene-1,8(2H)-dione

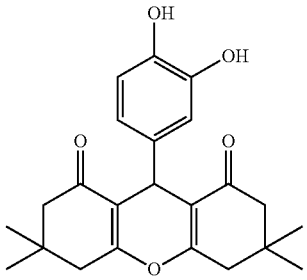

$^1$H NMR (400 MHz, DMSO d6): δ: 0.91 (s, 6H); 1.02 (s, 6H); 2.07 (d, syst.AB, 2H); 2.23 (d, syst.AB, 2H); 2.52 (m, 4H); 4.37 (s, 1H); 6.36 (d, 1H); 6.53 (d, 1H); 6.60 (s, 1H); 8,58 (s, OH, 1H); 8.7 (s, OH, 1H).

$^{13}$C NMR (100 MHz, DMSO d6): δ: 26.4; 28.6; 30.0; 31.7; 50.0; 114.8; 114.9; 115.8; 118.4; 135.3; 143.4; 144.4; 162.3; 195.9.

MS (APCI): 383.2 [M+H]$^+$

Rf (1/1; Heptane/EtOAc): 0.75

EXAMPLE 3

-9-(4-hydroxy-3,5-dimethoxyphenyl)-3,3,6,6-tetramethyl-3,4,5,6,7,9-hexahydro-1H-xanthene-1,8(2H)-dione

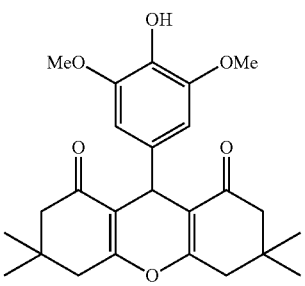

$^1$H NMR (400 MHz, DMSO d6): δ: 0.93 (s, 6H); 1.03 (s, 6H); 2.10 (d, syst.AB, 2H); 2.27 (d, syst.AB, 2H); 2.52 (m, 4H); 3.66 (s, 6H); 4.44 (s, 1H); 6.36 (s, 2H); 8.1 (s, OH, 1H).

$^{13}$C NMR (100 MHz, DMSO d6): δ: 26.1; 28.7; 30.6; 31.7; 49.9; 55.8; 105.6; 114.4; 124.9; 134.1;134.4; 147.4; 162.6; 196.0.

MS (ESI+): 427.2 [M+H]$^+$

EXAMPLE 4

-9-(3,4-dihydroxyphenyl)-3,6-diphenyl-3,4,5,6,7,9-hexahydro-1H-xanthene-1,8(2H)-dione

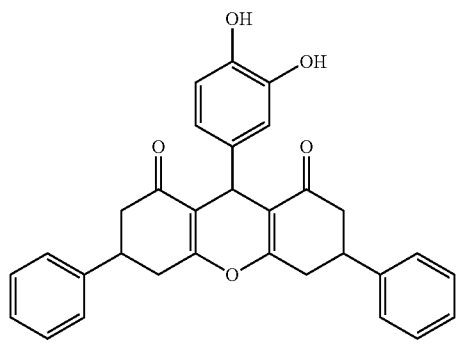 [SMILES: O=C1CC(c2ccccc2)CC2=C1C(c1ccc(O)c(O)c1)C1=C(CC(c3ccccc3)CC1=O)O2]

$^1$H NMR (400 MHz, CDCl$_3$): δ: 2.64 (m, 4H); 2.83 (m, 4H); 3.35 (m, 1H); 3.46 (m, 1H); 4.81 (s, 1H); 6.38-7.04 (m, 3H); 7.3 (m, 10H).

MS (APCI+): 479.1 [M+H]$^+$

Rf (cyclohexane/EtOAc; 1/1): 0.38

EXAMPLE 5

9-(3,5-di-tert-butyl-4-hydroxyphenyl)-3,3,6,6-tetramethyl-3,4,5,6,7,9-hexahydro-1H-xanthene-1,8(2H)-dione

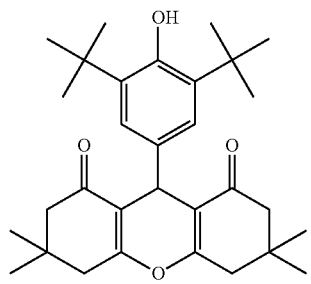

$^1$H NMR (400 MHz, CDCl$_3$): δ: 0.99 (s, 6H); 1.10 (s, 6H); 1.37 (s, 18H); 2.20 (dd, 4H); 2.45 (dd, 4H); 4.67 (s, 1H); 4.98 (d, 1H); 7.02 (s, 2H).

$^{13}$C NMR (100 MHz, CDCl$_3$): δ: 26.9; 29.4; 30.3; 31.0; 32.2; 34.1; 40.9; 50.7; 116.2; 124.8; 134.8; 134.9; 152.0; 162.0; 196.3.

MS (ESI+): 479.3 [M+H]$^+$

Rf (heptane/EtOAc; 7/3): 0.26

EXAMPLE 6

9-(4-hydroxy-3-methoxyphenyl)-3,6-diphenyl-3,4,5,6,7,9-hexahydro-1H-xanthene-1,8(2H)-dione

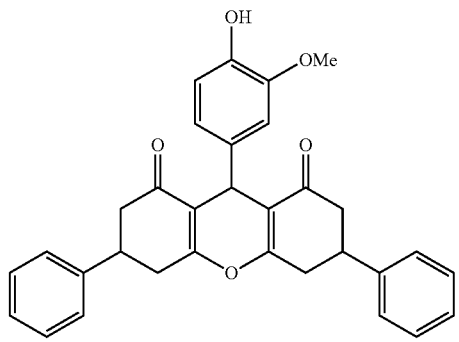

$^1$H NMR (400 MHz, CDCl$_3$): δ: 2.66 (m, 4H); 2.87 (m, 4H); 3.30 (m, 1H); 3.48 (m, 1H); 3.84 (s, 3H); 4.81 (s, 1H); 5.57 (s, 1H); 6.43-6.83 (m, 3H); 7.09-7.36 (m, 10H).

MS (ESI+): 515.0 [M+Na]$^+$

Rf (cyclohexane/EtOAc; 1/1): 0.51

EXAMPLE 7

-(9Z,12Z)-2-methoxy-4-(3,3,6,6-tetramethyl-1,8-dioxo-2,3,4,5,6,7,8,9-octahydro-1H-xanthen-9-yl)phenyl octadeca-9,12-dienoate

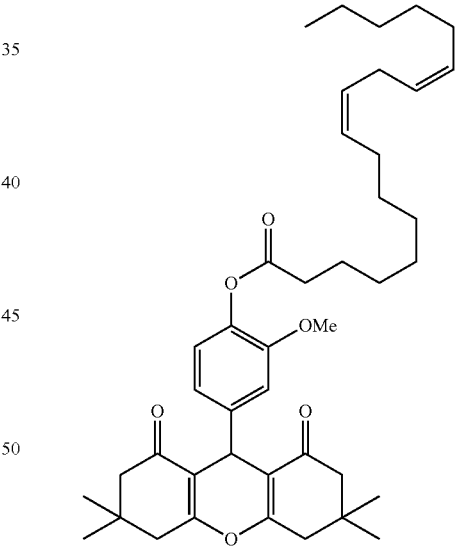

To a solution of 0.99 g of xanthenedione (example 1) (2.5 mmol) in 12.5 mL of anhydrous DCM under N$_2$ are added 417 µL of triethylamine (3 mmol). The mixture is cooled to 0° C. by an ice bath, then 0.88 mL of linoleic acid chloride are added drop by drop. After 5 minutes of stirring at 0° C., the ice bath is removed and the reaction is continued at ambient temperature overnight. The mixture is extracted with distilled water and washed with a saturated solution of NaCl before drying the organic phase with MgSO$_4$, which is then filtered. The solution is evaporated to dryness to obtain a yellow oil and a combiflash is carried out. A gradient of 95:5 to 50:50 in heptane/ethyl acetate is used. The pure fraction is recovered and evaporated.

The solid is dried in the oven for at least 30 minutes under 50 mbar in order to obtain 1.26 g of beige product with a yield of 76.5%.

$^1$H NMR (400 MHz, CDCl$_3$): δ: 0.88 (t, 3H); 1.01 (s, 6H); 1.10 (s, 6H); 1.30 (m, 14H); 1.72 (m, 2H); 2.05 (m, 4H); 2.17 (m, 4H); 2.45 (s, 4H); 2.53 (m, 2H); 2.77 (t, 2H); 3.81 (s, 3H); 4.76 (s, 1H); 5.30 (m, 4H); 6.70 (dd, 1H); 6.74 (d, 1H); 7.04 (d, 1H).

$^{13}$C NMR (100 MHz, CDCl$_3$): δ: 14.03; 22.51; 24.94; 25.56; 27.14; 27.35; 28.94; 29.09; 29.13; 29.17; 29.28; 29.55; 31.35; 31.45; 31.97; 32.15; 32.30; 33.96; 40.81; 50.66; 55.78; 76.68; 77.00; 77.32.

MS (ESI+): 659.4 [M+H]$^+$

Rf (cyclohexane/EtOAc; 2/1): 0.52

EXAMPLE 8

2-methoxy-4-(3,3,6,6-tetramethyl-1,8-dioxo-2,3,4,5,6,7,8,9-octahydro-1H-xanthen-9-yl)phenyl palmitate

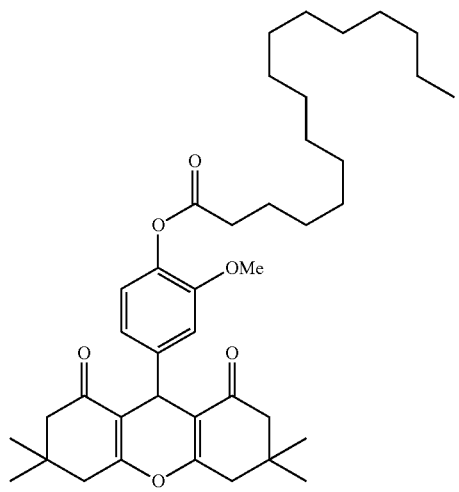 [SMILES: CCCCCCCCCCCCCCCC(=O)Oc1ccc(C2C3=C(CC(C)(C)CC3=O)OC3=C2C(=O)CC(C)(C)C3)cc1OC]

Same protocol as for example 7 from palmitoyl chloride.

$^1$H NMR (400 MHz, CDCl$_3$): δ: 0.89 (t, 3H); 1.00 (s, 6H); 1.10 (s, 6H); 1.31 (m, 22H); 1.39 (m, 2H); 1.72 (m, 4H); 2.22 (m, 4H); 2.45 (m, 4H); 3.81 (s, 3H); 4.66 (s, 1H); 6.69 (dd, 1H); 6.84 (d, 1H); 7.04 (d, 1H).

MS (ESI+): 652.5 [M+NH$_4$]$^+$

Rf (heptane/EtOAc; 1/1): 0.54

EXAMPLE 9

9-(4-hydroxyphenyl)-3,3,6,6-tetramethyl-3,4,5,6,7,9-hexahydro-1H-xanthene-1,8(2H)-dione

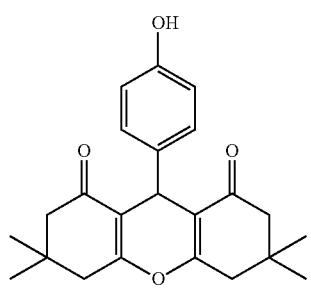

$^1$H NMR (400 MHz, CDCl$_3$): δ: 0.99 (s, 6H); 1.09 (s, 6H); 2.20 (m, 4H); 2.46 (s, 4H); 4.66 (s, 1H); 5.83 (s, 1H); 6.54 (d, 2H); 7.07 (d, 2H).

$^{13}$C NMR (100 MHz, CDCl$_3$): δ: 27.33; 29.09; 30.89; 32.21; 40.79; 50.70; 115.22; 115.82; 129.26; 135.41; 154.74; 162.43; 197.28.

MS (ESI+): 367.2 [M+H]$^+$

Rf (cyclohexane/EtOAc; 1/1): 0.58

EXAMPLE 10

-9-(4-hydroxy-3,5-dimethylphenyl)-3,3,6,6-tetramethyl-3,4,5,6,7,9-hexahydro-1H-xanthene-1,8(2H)-dione

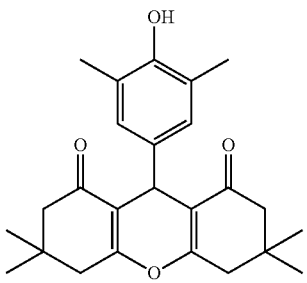

$^1$H NMR (400 MHz, CDCl$_3$): δ: 0.99 (s, 6H); 1.09 (s, 6H); 2.05 (s, 6H); 2.20 (s, 4H); 2.46 (s, 4H); 4.60 (s, 1H); 5.00 (s, 1H); 6.83 (s, 2H).

$^{13}$C NMR (100 MHz, CDCl$_3$): δ: 15.95; 27.31; 29.15; 30.85; 32.19; 40.82; 50.77; 115.90; 122.56; 128.43; 135.49; 150.79; 161.96; 196.72.

MS (ESI+): 395.2 [M+H]$^+$

Rf (cyclohexane/EtOAc; 1/1): 0.64

EXAMPLE 11

-9-(4-hydroxy-3-methoxyphenyl)-3,4,5,6,7,9-hexahydro-1H-xanthene-1,8(2H)-dione

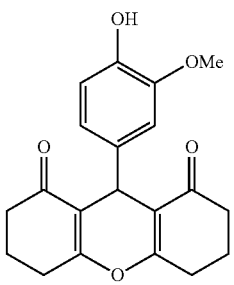 [SMILES: COc1cc(C2C3=C(CCCC3=O)OC3=C2C(=O)CCC3)ccc1O]

$^1$H NMR (400 MHz, CDCl$_3$): δ: 2.00 (m, 4H); 2.33 (m, 4H); 2.60 (m, 4H); 3.87 (s, 3H); 4.73 (s, 1H); 5.49 (s, 1H); 6.53 (dd, 1H); 6.73 (d, 1H); 7.07 (d, 1H).

MS (ESI+): 358.2 [M+NH$_4$]$^+$

Rf (cyclohexane/EtOAc; 3/7): 0.39

EXAMPLE 12

-9-(4-hydroxy-3-methoxyphenyl)-3,6-diisopropyl-3,4,5,6,7,9-hexahydro-1H-xanthene-1,8(2H)-dione

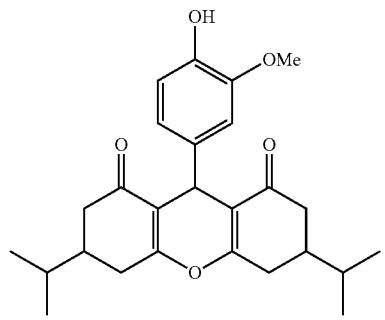 [SMILES: COc1cc(C2C3=C(CC(C(C)C)CC3=O)OC3=C2C(=O)CC(C(C)C)C3)ccc1O]

$^1$H NMR (400 MHz, CDCl$_3$): δ: 0.92 (m, 12H); 1.60 (m, 2H); 1.70 (m, 2H); 2.10 (m, 2H); 2.30 (m, 2H); 2.45 (m, 2H); 2.65 (m, 2H); 3.88 (s, 3H); 4.70 (s, 1H); 5.62 (s, 1H); 6.51 (m, 1H); 6.72 (m, 1H); 7.07 (m, 1H).

MS (ESI+): 425.2 [M+H]$^+$

Rf (cyclohexane/EtOAc; 1/1): 0.65

EXAMPLE 13

-3,6-bis(4-fluorophenyl)-9-(4-hydroxy-3-methoxyphenyl)-3,4,5,6,7,9-hexahydro-1H-xanthene-1,8(2H)-dione

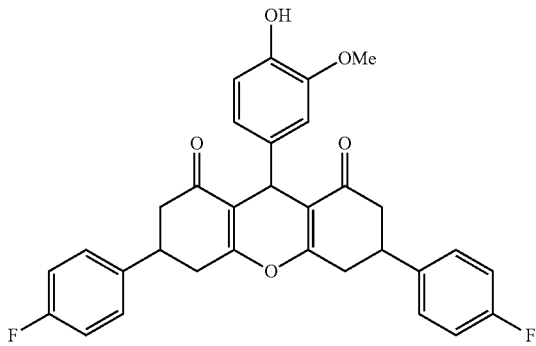 [SMILES: COc1cc(C2C3=C(CC(c4ccc(F)cc4)CC3=O)OC3=C2C(=O)CC(c2ccc(F)cc2)C3)ccc1O]

$^1$H NMR (400 MHz, CDCl$_3$): δ: 2.30 (m, 4H); 2.78 (m, 4H); 3.00 (m, 1H); 3.40 (m, 1H); 3.54 (s, 1H); 3.84 (m, 3H); 5.50 (s, 1H); 6.40 (m, 1H); 6.68 (m, 1H); 6.90 (m, 1H); 7.08 (m, 4H); 7.25 (m, 4H).

MS (ESI+): 547.2 [M+NH$_4$]$^+$

Rf (cyclohexane/EtOAc; 1/1): 0.50

EXAMPLE 14

-3,6-bis(3,4-dimethoxyphenyl)-9-(4-hydroxy-3-methoxyphenyl)-3,4,5,6,7,9-hexahydro-1H-xanthene-1,8(2H)-dione

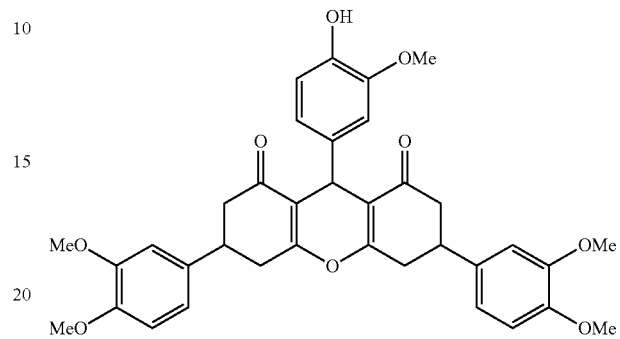

$^1$H NMR (400 MHz, CDCl$_3$): δ: 2.65 (m, 4H); 2.87 (m, 4H); 3.31 (m, 1H); 3.47 (m, 1H); 3.85 (m, 15H); 4.80 (m, 1H); 5.53 (s, 1H); 6.50 (m, 1H); 6.70 (m, 6H); 7.10 (m, 1H); 7.30 (m, 1H).

MS (ESI+): 630.3[M+NH$_4$]$^+$

Rf (cyclohexane/EtOAc; 3/7): 0.42

EXAMPLE 15

-9-(3-ethoxy-4-hydroxyphenyl)-3,3,6,6-tetramethyl-3,4,5,6,7,9-hexahydro-1H-xanthene-1,8(2H)-dione

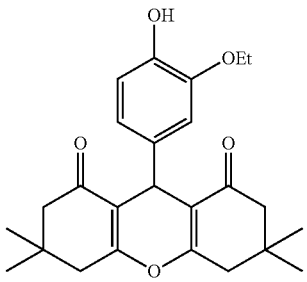

$^1$H NMR (400 MHz, CDCl$_3$): δ: 0.99 (s, 6H); 1.09 (s, 6H); 1.40 (t, 3H); 2.20 (m, 4H); 2.46 (s, 4H); 4.13 (s, 2H); 4.64 (s, 1H); 5.56 (s, 1H); 6.56 (dd, 1H); 6.73 (d, 1H); 6.98 (d, 1H).

$^{13}$C NMR (100 MHz, CDCl$_3$): δ: 14.79; 27.21; 29.22; 31.21; 32.11; 40.76; 50.69; 64.22; 113.05; 113.78; 115.71; 119.82; 136.26; 144.02; 145.07; 162.00; 196.52.

MS (ESI+): 411.2 [M+H]$^+$

Rf (cyclohexane/EtOAc; 1/1): 0.50

EXAMPLE 16

-9-(3-chloro-4-hydroxy-5-methoxyphenyl)-3,3,6,6-tetramethyl-3,4,5,6,7,9-hexahydro-1H-xanthene-1,8(2H)-dione

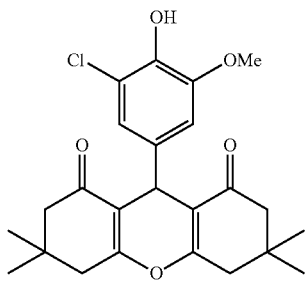

$^1$H NMR (400 MHz, CDCl$_3$): δ: 1.00 (s, 6H); 1.10 (s, 6H); 2.20 (m, 4H); 2.47 (s, 4H); 3.90 (s, 3H); 4.64 (s, 1H); 5.73 (s, 1H); 6.61 (d, 1H); 6.97 (d, 1H).

$^{13}$C NMR (100 MHz, CDCl$_3$): δ: 27.34; 29.18; 31.33; 32.20; 40.80; 50.71; 56.29; 111.18; 115.21; 118.82; 120.41; 136.59; 140.44; 146.72; 162.37; 196.55.

MS (ESI+): 431.1 [M+H]$^+$

Rf (cyclohexane/EtOAc; 1/1): 0.48

EXAMPLE 17

-9-(3-bromo-4-hydroxy-5-methoxyphenyl)-3,3,6,6-tetramethyl-3,4,5,6,7,9-hexahydro-1H-xanthene-1,8(2H)-dione

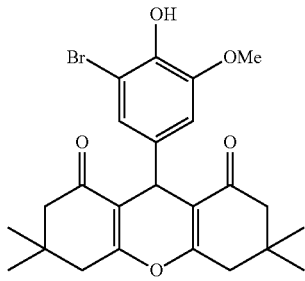

$^1$H NMR (400 MHz, CDCl$_3$): δ: 1.00 (s, 6H); 1.10 (s, 6H); 2.20 (m, 4H); 2.47 (s, 4H); 3.90 (s, 3H); 4.64 (s, 1H); 5.80 (s, 1H); 6.74 (d, 1H); 7.01 (d, 1H).

$^{13}$C NMR (100 MHz, CDCl$_3$): δ: 27.31; 29.17; 31.25; 32.19; 40.78; 50.69; 56.26; 107.57; 111.84; 115.19; 123.17; 137.19; 141.50; 146.50; 162.36; 196.55.

MS (ESI+): 475.0 [M+H]$^+$

Rf (cyclohexane/EtOAc; 1/1): 0.37

EXAMPLE 18

-9-(4-hydroxy-3-iodo-5-methoxyphenyl)-3,3,6,6-tetramethyl-3,4,5,6,7,9-hexahydro-1H-xanthene-1,8(2H)-dione

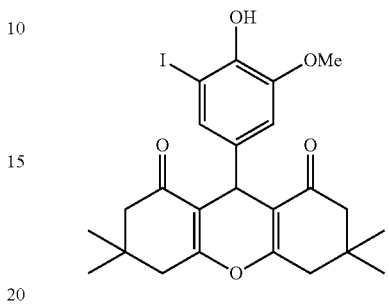

$^1$H NMR (400 MHz, CDCl$_3$): δ: 1.00 (s, 6H); 1.10 (s, 6H); 2.20 (m, 4H); 2.47 (s, 4H); 3.89 (s, 3H); 4.61 (s, 1H); 6.00 (s, 1H); 6.92 (d, 1H); 7.04 (d, 1H).

$^{13}$C NMR 100 MHz, CDCl$_3$): δ: 27.25; 29.19; 31.03; 32.18; 40.76; 50.67; 56.15; 80.60; 112.78; 115.20; 128.93; 138.05; 144.07; 145.35; 162.30; 196.54.

MS (ESI+): 523.1 [M+H]$^+$

Rf (cyclohexane/EtOAc; 1/1): 0.47

EXAMPLE 19

-9-(3,4-dihydroxy-5-methoxyphenyl)-3,3,6,6-tetramethyl-3,4,5,6,7,9-hexahydro-1H-xanthene-1,8(2H)-dione

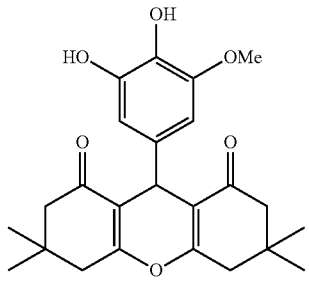

$^1$H NMR (400 MHz, CDCl$_3$): δ: 1.00 (s, 6H); 1.10 (s, 6H); 2.17 (m, 4H); 2.45 (s, 4H); 3.85 (s, 3H); 4.64 (s, 1H); 5.47 (s, 2H); 6.31 (d, 1H); 6.65 (d, 1H).

$^{13}$C NMR (100 MHz, CDCl$_3$): δ: 27.40; 29.06; 31.33; 32.10; 40.73; 50.66; 55.97; 104.89; 107.54; 115.55; 131.04; 135.94; 143.68; 146.35; 162.23; 196.84.

MS (ESI+): 413.2 [M+H]$^+$

Rf (cyclohexane/EtOAc; 3/7): 0.66

EXAMPLE 20

-(3R,4S,5S)-2-(acetoxymethyl)-6-(2-methoxy-4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate

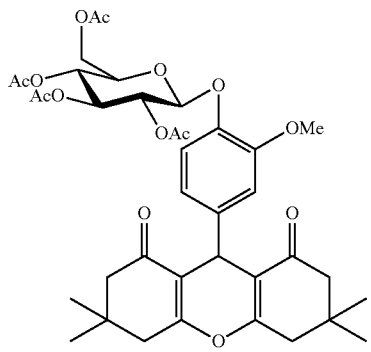

Product obtained according to the general procedure A from glucosylated vanillin, the synthesis of which is described in the literature (*Chemical and pharmaceutical bulletin*, 51(11), 1268-1272; 2003).

The product is obtained after purification on silica in the form of a white solid.

$^1$H NMR (400 MHz, CDCl$_3$): δ: 0.97 (s, 3H); 1.02 (s, 3H); 1.10 (s, 3H); 1.11 (s, 3H); 2.02 (s, 3H); 2.03 (s, 3H); 2.05 (s, 3H); 2.06 (s, 3H); 2.21 (m, 4H); 2.45 (m, 4H); 3.71 (m, 1H); 3.81 (s, 3H); 4.11 (dd, 1H); 4.25 (dd, 1H); 4.69 (s, 1H); 4.88 (d, 1H); 5.13 (dd, 1H); 5.24 (m, 2H); 6.64 (dd, 1H); 6.92 (d, 1H); 6.99 (d, 1H).

$^{13}$C NMR (100 MHz, CDCl$_3$): δ: 20.56; 20.61; 20.68; 26.85; 27.13; 27.30; 29.25; 31.47; 32.12; 32.15; 40.79; 50.67; 50.70; 55.94; 61.86; 68.40; 71.14; 71.69; 72.60; 100.69; 113.85; 115.33; 115.54; 119.74; 120.05; 140.99; 144.29; 150.09; 162.13; 162.46; 169.38; 169.39; 170.23; 170.61; 196.42; 196.64.

MS (APCI+): 727.2 [M+H]$^+$

EXAMPLE 21

-9-(3-methoxy-4-((3S,4S,5S)-3,4,5-trihydroxy-6-(hydroxymethyl)tetrahydro-2H-pyran-2-yloxy)phenyl)-3,3,6,6-tetramethyl-3,4,5,6,7,9-hexahydro-1H-xanthene-1,8(2H)-dione

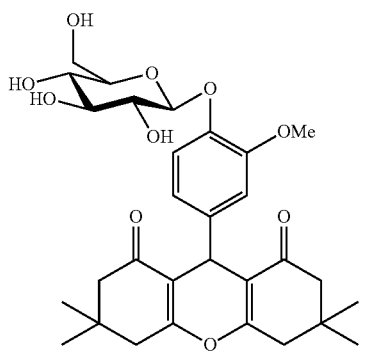

A solution of the example 20 in anhydrous methanol is treated by a solution of sodium methylate according to the procedure described in the following reference. The product is then obtained in the form of a white solid. (*European Journal of Medicinal Chemistry* 43 (2008) 2549-2556)

$^1$H NMR (300 MHz, CD3OD): δ: 1.00 (s, 6H); 1.12 (s, 6H); 2.17 (d, 2H); 2.33 (d, 2H); 2.58 (2d, 4H); 3.36 (m, 2H); 3.39 (m, 2H); 3.70 (m, 1H); 3.85 (m, 1H); 3.87 (s, 3H); 4.60 (s, 1H); 4.82 (d, 1H); 6.73 (d, 1H); 6.97 (s, 1H); 7.03 (d, 1H).

MS (ESI+): 581.1 [M+Na]$^+$

EXAMPLE 22

-(3S,4S,5S,6S)-2-(acetoxymethyl)-6-(2-methoxy-4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate

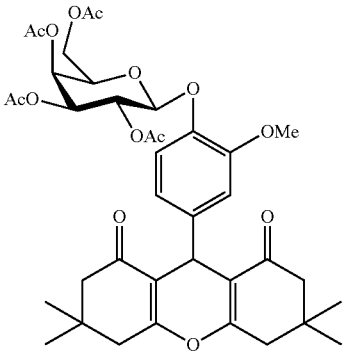

Product obtained according to the procedure described for example 20 from galactosylated vanillin, the synthesis of which is described in the literature (*European Journal of Medicinal Chemistry*, 43 (2008) 166-173)

The product is obtained after purification on silica in the form of a white solid.

$^1$H NMR (400 MHz, CDCl$_3$): δ: 0.97 (s, 3H); 1.02 (s, 3H); 1.10 (s, 3H); 1.11 (s, 3H); 2.00 (s, 3H); 2.02 (s, 3H); 2.07 (s, 3H); 2.15 (s, 3H); 2.21 (m, 4H); 2.45 (m, 4H); 3.81 (m, 1H); 3.92 (t, 1H); 4.12 (m, 1H); 4.69 (s, 1H); 4.83 (d, 1H); 5.06 (dd, 1H); 5.43 (m, 2H); 6.63 (dd, 1H); 6.92 (d, 1H); 6.99 (d, 1H).

MS (APCI+): 727.4 [M+H]$^+$, 744.4 [M+NH$_4$]$^+$.

EXAMPLE 23

-9-(3-methoxy-4-((2S,3S,4S,5R)-3,4,5-trihydroxy-6-(hydroxymethyl)tetrahydro-2H-pyran-2-yloxy)phenyl)-3,3,6,6-tetramethyl-3,4,5,6,7,9-hexahydro-1H-xanthene-1,8(2H)-dione

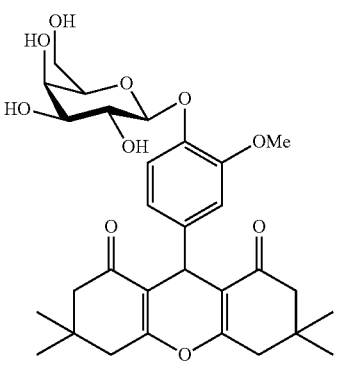

A solution of example 22 in anhydrous methanol is treated by a solution of sodium methylate according to the procedure described in the following reference. The product is then obtained in the form of a white solid. (*European Journal of Medicinal Chemistry*, 43 (2008) 2549-2556)

$^1$H NMR (400 MHz, CDCl$_3$): δ: 0.92 (s, 6H); 1.15 (s, 6H); 2.09 (dd, 2H); 2.11 (dd, 2H); 2.54 (m, 4H); 3.57 (m, 3H); 3.68 (s, 3H); 4.47 (m, 2H); 4.62 (t, 1H); 4.80 (dd, 2H); 4.98 (d, 1H); 6.63 (dd, 1H); 6.72 (d, 1H); 6.91 (d, 1H).

EXAMPLE 24

-(3R,4S,5S,6S)-2-(acetoxymethyl)-6-(4-(3,3,6,6-tetramethyl-1,8-dioxo-2,3,4,5,6,7,8,9-octahydro-1H-xanthen-9-yl)phenoxy)tetrahydro-2H-pyran-3,4,5-triyltriacetate

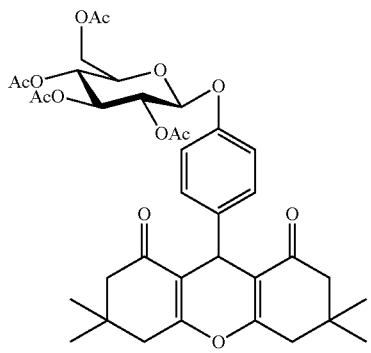

Product obtained according to the general procedure from glucosylated vanillin, the synthesis of which is described in the literature (*Chemical and pharmaceutical bulletin*, 51(11), 1268-1272; 2003).

The product is obtained after purification on silica in the form of a white solid.

$^1$H NMR (400 MHz, CDCl$_3$): δ: 0.98 (s, 6H); 1.10 (s, 6H); 2.02 (s, 3H); 2.03 (s, 3H); 2.05 (s, 3H); 2.06 (s, 3H); 2.20 (m, 4H); 2.45 (m, 4H); 3.81 (m, 1H); 4.13 (dd, 1H); 4.28 (dd, 1H); 4.70 (s, 1H); 5.01 (d, 1H); 5.14 (dd, 1H); 5.24 (m, 2H); 6.83 (d, 2H); 7.21 (d, 2H).

MS (ESI+): 697.3 [M+H]$^+$; 714.3 [M+NH4]$^+$.

EXAMPLE 25

-3,3,6,6-tetramethyl-9-(4-((2S,3S,4S,5S)-3,4,5-trihydroxy-6-(hydroxymethyl)tetrahydro-2H-pyran-2-yloxy)phenyl)-3,4,5,6,7,9-hexahydro-1H-xanthene-1,8(2H)-dione

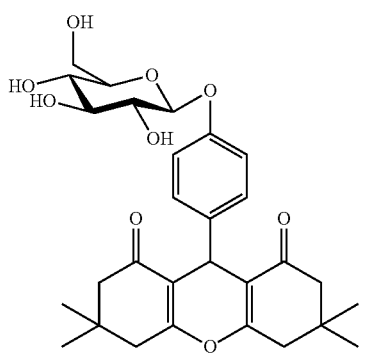

A solution of example 24 in anhydrous methanol is treated by a solution of sodium methylate according to the procedure described in the following reference. The product is then obtained in the form of a white solid. (*European Journal of Medicinal Chemistry*, 43 (2008) 2549-2556)

$^1$H NMR (300 MHz, CD3OD): δ: 0.88 (s, 6H); 1.0 (s, 6H); 2.20 (d, 2H); 2.42 (d, 2H); 2.52 (2d, 4H); 3.20 (m, 2H); 3.28 (m, 4H); 3.57 (dd, 1H); 3.76 (d, 1H); 4.49 (s, 1H); 4.73 (d, 1H); 6.84 (d, 2H); 7.06 (d, 1H).

$^{13}$C NMR (75 MHz, CD3OD): δ: 27.7; 27.8; 29.8; 29.9; 32.7; 33.6; 41.8; 51.9; 62.9; 71.7; 75.3; 78.3; 78.4; 102.7; 117.0; 117.6; 130.9; 140.0; 158.0; 165.4; 199.7.

MS (ESI+): 529.3 [M+H]$^+$; 546.3 [M+NH4]$^+$; 551.2 [M+Na]$^+$.

EXAMPLE 26

4-(1,8-dioxo-3,6-diphenyl-2,3,4,5,6,7,8,9-octahydro-1H-xanthen-9-yl)-1,2-phenylene diacetate

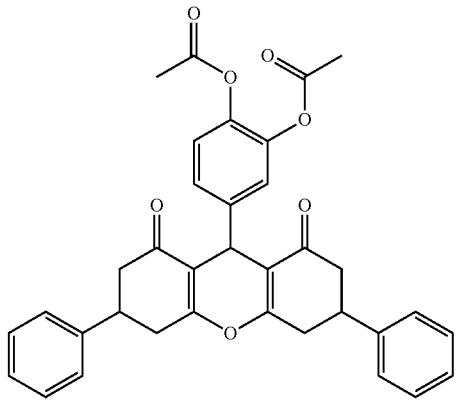 [SMILES: CC(=O)Oc1ccc(C2C3=C(CC(c4ccccc4)CC3=O)OC3=C2C(=O)CC(c2ccccc2)C3)cc1OC(C)=O]

prepared from 3,4-diacetoxybenzaldehyde.

$^1$H NMR (400 MHz, CDCl$_3$): δ: 2.27 (s, 6H); 2.30 (m, 4H); 2.83 (m, 4H); 3.4 (m, 1H); 3.5 (m, 1H); 4.93 (s, 1H); 7.04 (m, 3H); 7.3 (m, 10H).

MS (ESI+): 563.2 [M+H]$^+$

Rf (cyclohexane/EtOAc; 1/1): 0.40

EXAMPLE 27

-4-(3,3,6,6-tetramethyl-1,8-dioxo-2,3,4,5,6,7,8,9-octahydro-1H-xanthen-9-yl)-1,2-phenylene diacetate

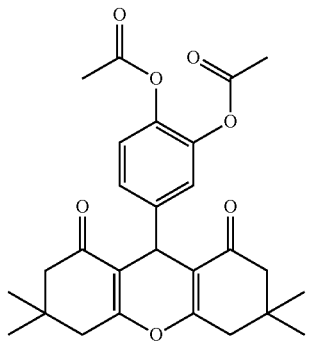

prepared from 3,4-diacetoxybenzaldehyde.

$^1$H NMR (400 MHz, CDCl$_3$): δ: 0.99 (s, 6H); 1.09 (s, 6H); 1.88 (s, 3H); 2.22 (m, 4H); 2.46 (s, 4H); 4.77 (s, 1H); 7.04 (dd, 1H); 7.20 (d, 1H); 7.22 (d, 1H).

$^{13}$C NMR (100 MHz, CDCl$_3$): δ: 20.62; 27.46; 29.04; 31.08; 32.17; 40.77; 50.59; 115.03; 122.62; 122.88; 126.55; 140.34; 141.61; 142.58; 162.50; 167.91; 168.16; 196.50.

MS (ESI+): 467.1 [M+H]$^+$

Rf (cyclohexane/EtOAc; 3/7): 0.38

2) Experimental Test Protocol

A) Melanin Assay Test in B16-F10 Cells:
Principle:
This involves a test of measuring the synthesis of melanin by colorimetric assay on a murine melanoma cell line: the B16-F10 line. This test enables the depigmenting power of active ingredients to be evaluated.

The B16-F10 cells are cultured in 96-well plates in DMEM medium, supplemented with FCS (foetal calf serum), and incubated 24 hours at 37° C., 5% CO$_2$. The cells are then stimulated with 0.1 μM α-MSH (to stimulate the synthesis of melanin, the stimulation observed is around 150%) and treated 72 hours with the active ingredients to be tested. Each concentration of active ingredient is tested at least in triplicate. The total melanin followed by the intracellular melanin dissolved in the lysis buffer are then assayed by absorbance reading at 405 nm. The total proteins are assayed in the lysate and the results are expressed in mg melanin/mg proteins. The percentage of activity is calculated as follows:

% activity =

$$\frac{\text{Normalised average of control} - \text{Normal average of treated}}{\text{Normalised average of control}} \times 100$$

A negative value indicates an inhibition, whereas a positive value indicates an induction of the synthesis of melanin.
General Experimental Conditions:
  Equipment:
    CO2 cell incubator (Heraeus), Oven, Centrifuge (Heraeus), Laminar air flow fume hood, 96-well clear bottomed plates—Falcon, sterile cones—Treff Lab, Polylabo, Mithras LB940 (Berthold Technologies)-154/MIPA/003
Biological Equipment:
  B16-F10 cell line between P10 and P20 (murine melanocytes) (ATCC, CRL-6475)
Reagents
  DMEM without phenol red (G$_{IBCO}$BRL, 31053-028), 200 mM Glutamax-I Supplement (G$_{IBCO}$BRL, 35050-038), D-PBS (G$_{IBCO}$BRL, 14190-094), Foetal calf serum (Invitrogen, 10270-098), Trypsine-EDTA (G$_{IBCO}$BRL, 25300-054), NaOH (Sigma, S8045-500G), DMSO (Sigma, 471267-1L), Nle, Phe—Melanocyte Stimulating Hormone (Sigma, M-8764), Melanin (Sigma, M-0418), BCA-C$_{OPPER}$ (S$_{IGMA}$, B9643 $_{AND}$ C2284), BSA (S$_{IGMA}$, P0914)
B) Test for the Study of the Antioxidant Capacity by Chemiluminescence (Photochem Analytik Jena)
Principle:
This test is used to determine the antioxidant capacity of molecules. It is a method that generates free radicals by a photochemical signal. The intensity of the oxidation is 1000 times greater than those obtained under normal conditions.

The detection is performed by chemiluminescence. It enables the evaluation of hydrosoluble and liposoluble antioxidant molecules or extracts.

The results are expressed respectively in equivalent quantity of vitamin C or Trolox (6-hydroxy-2,5,7,8-tetramethyl-chroman-2-carboxylic acid). The sensitivity is of the order of the nanomole.

The antioxidant activity studied in this test represents the capacity to specifically trap the superoxide anions by chemiluminescence.

The quantified results are expressed in equivalent Trolox (standard), i.e. in "μg of product for 1 μg of Trolox". This signifies that a quantity x of sample is required to obtain an activity equivalent to the activity detected for 1 μg of standard. It is an anti-oxidant power relative to a reference, which can be determined independently of the tested concentration.
Generation of Oxygenated Free Radicals:
The superoxide radical: $O_2^{°-}$ is generated by a photochemical reaction:

$$L + h\nu(UV) + O_2 \rightarrow L*O_2 \rightarrow L^{°+} + O_2^{°-}$$

L*: luminol in the excited state
L$^{°+}$: luminol radical
Detection of the Signal:
Part of the superoxide anions is quenched by anti-oxidants. The remaining free radicals are quantified by chemiluminescence.

$$L^{°+} + O_2^{°-} \rightarrow N2 + SP^{*2-} \rightarrow AP^{2-} + h\nu(luminescence)$$

AP$^{*2-}$: aminophthalate in the excited state

| Name | Conditions | Photosensitising | Antioxidant |
|---|---|---|---|
| Blank | 100% $O_2^{°-}$ generated | + | − |
| Standards | Standard range: From 1 to 3 nmol | + | Vitamin C or Trolox |
| Test | +/− $O_2^{°-}$ generated | + | Molecule x to be tested |

3) Experimental Test Results

A) Melanin Assay Test in B16-F10 cells:
The results are shown in summary Table 1 below.
Interpretation of Results:
IC50 represents the concentration for which 50% melanin synthesis inhibition is observed.

It may be observed that the majority of compounds tested have good melanin synthesis inhibition capacity. The compounds according to the invention have good depigmenting activity.
B) Test for the Study of the Antioxidant Capacity by Chemiluminiscence (Photochem Analytik Jena)
The results are also given in summary Table 1 below.
The majority of the compounds have good antioxidant activity. The scale for interpreting the results is the following:

| Products | μg sample for 1 μg of Trolox | Activity |
|---|---|---|
| Vitamin C | 0.1 to 3.0 | Very good |
| BHT | 3.01 to 50 | Good |
| Cysteine | 50.1 to 1000 | Medium |
| Albumin | >1000 | Low |
| Lipoic acid | Negative | Nil |

Most of the compounds have results comparable to vitamin C. All of the compounds show results below 1000 μg of Trolox (74 μg being the lowest result obtained with example 30); thus, they all have worthwhile anti-oxidant activity.

This antioxidant activity of the compounds that are the object of the present invention, objectified by the trapping of free radicals, has also made it possible to propose their use in the treatment and/or the prevention of inflammations of the skin ("Free radicals in inflammation: second messengers and mediators of tissue destruction", V. R. Winrow et al. http://bmb.oxfordjournals.org/cgi/content/abstract/49/3/506).

TABLE 1

Results of the experimental tests

| Example | Structure | Results activity $B_{16-F10}$ $IC_{50}$ | μg of sample for 1 μg of Trolox |
|---|---|---|---|
| Example 1 | 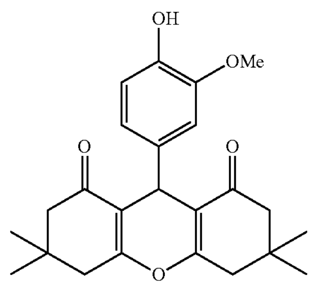 | 50 μM | 2.1 |
| Example 2 | 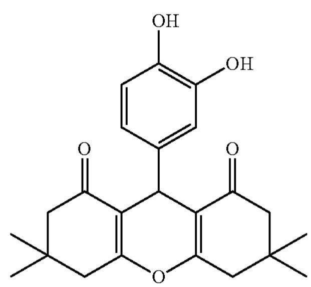 | 20 μM | 0.03 |
| Example 3 | 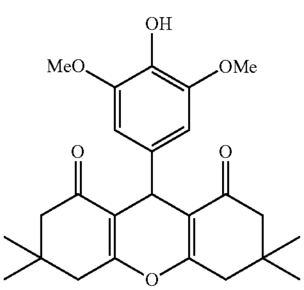 | 45 μM | 0.72 |
| Example 4 | 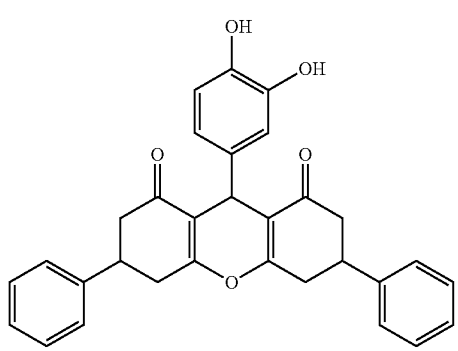 [SMILES: O=C1CC(c2ccccc2)CC2=C1C(c1ccc(O)c(O)c1)C1=C(CC(c3ccccc3)CC1=O)O2] | 7 μM | 0.001 |

TABLE 1-continued
Results of the experimental tests
| Example | Structure | Results activity $B_{16\text{-}F10}$ $IC_{50}$ | µg of sample for 1 µg of Trolox |
|---|---|---|---|
| Example 5 | 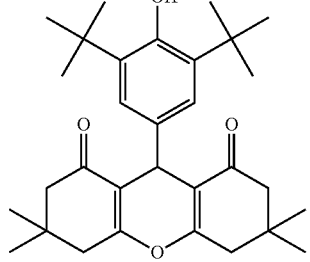 | 2 µM | 50 |
| Example 6 | 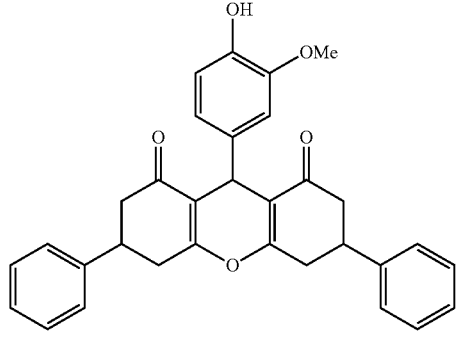 | 6 µM | 2.46 |
| Example 7 | 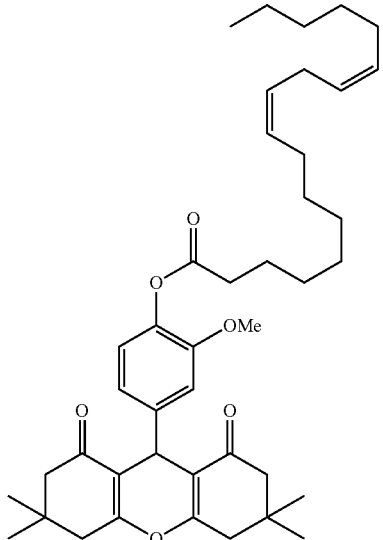 [SMILES: CCCCC/C=C\C/C=C\CCCCCCCC(=O)Oc1ccc(C2C3=C(CC(C)(C)CC3=O)OC3=C2C(=O)CC(C)(C)C3)cc1OC] | — | 19.7 |

TABLE 1-continued
Results of the experimental tests
| Example | Structure | Results activity $B_{16\text{-}F10}$ $IC_{50}$ | μg of sample for 1 μg of Trolox |
|---|---|---|---|
| Example 8 | 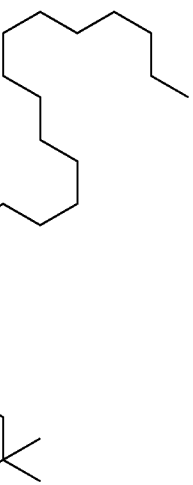 | — | — |
| Example 9 | 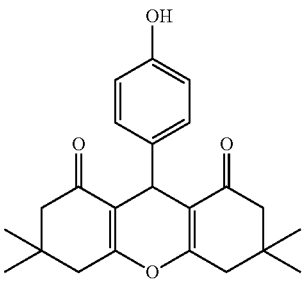 | 37 μM | 7.39 |
| Example 10 | 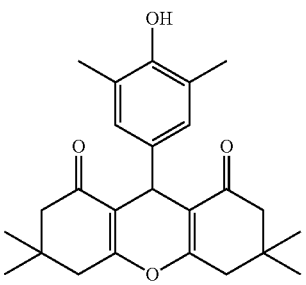 | — | 4.10 |
| Example 11 | 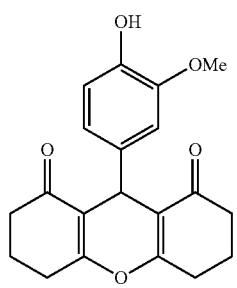 [SMILES: COc1cc(C2C3=C(CCCC3=O)OC3=C2C(=O)CCC3)ccc1O] | — | 1.07 |

TABLE 1-continued

Results of the experimental tests

| Example | Structure | Results activity B$_{16\text{-}F10}$ IC$_{50}$ | µg of sample for 1 µg of Trolox |
|---|---|---|---|
| Example 12 | | 16 µM | 1.64 |
| Example 13 | | — | 2.52 |
| Example 14 | | — | 2.27 |
| Example 15 | | 19 µM | 1.79 |

TABLE 1-continued

Results of the experimental tests

| Example | Structure | Results activity $B_{16\text{-}F10}$ $IC_{50}$ | μg of sample for 1 μg of Trolox |
|---|---|---|---|
| Example 16 | (structure) | −31% to 20 μM | 5.20 |
| Example 17 | (structure) | — | 5.18 |
| Example 18 | (structure) | — | 4.66 |
| Example 19 | (structure) | −22% to 10 μM | 0.02 |
| Example 20 | (structure) | — | — |

TABLE 1-continued

Results of the experimental tests

| Example | Structure | Results activity $B_{16\text{-}F10}$ $IC_{50}$ | μg of sample for 1 μg of Trolox |
|---|---|---|---|
| Example 21 | [structure] | 69 μM | — |
| Example 26 | [structure] | −28% to 20 μM | — |
| Example 27 | [structure] | — | 0.096 |

C) Test of Reconstructed Epidermises for the Study of Depigmenting Activity

The compounds of examples 8 and 21 were formulated at the concentration of 0.5% in a Simplex formula according to the example of composition A. Melanoderm-B (Black) or Melanoderm A (Asian) (MatTek, USA) reconstructed epidermis models were used. The reference compound chosen is kojic acid titrated to 2% in aqueous solution. The culture medium is changed every day. The products are applied by topical mode on the epidermis every two days. For the application, the epidermises are rinsed with PBS and the product to be tested is then applied.

A preliminary toxicity study made it possible to determine that the dose to apply for each treatment is 25 μL.

The morphology and the quantity of melanocytes in the tissue are not modified by the application of the products.

The tissues were observed on D3, D7, D10, D14 (Melanoderm B) or D6, D10, D14 and D21 (Melanoderm A) by 3 independent experts.

Simplex Composition A Formula

| Code | Nom commercial | Quantité g/100 g |
|---|---|---|
| 1 | Eau purifiée | 65.55 |
| 2 | Finsolv TN | 10 |
| 3 | Myritol 318 | 10 |
| 4 | Paraffine liquide 352 | 5 |
| 5 | Arlacel 165 | 5 |

-continued

| Code | Nom commercial | Quantité g/100 g |
|---|---|---|
| 6 | Propylène glycol | 3 |
| 7 | Sépiplus 400 | 1.25 |
| 8 | Actif | 0 |
| 9 | EDTA 2 Na | 0.2 |

| Code | Trade name | Quantity g/100 g |
|---|---|---|
| 1 | Purified water | 65.55 |
| 2 | Finsolv TN | 10 |
| 3 | Myritol 318 | 10 |
| 4 | Liquid paraffin 352 | 5 |
| 5 | Arlacel 165 | 5 |
| 6 | Propylene glycol | 3 |
| 7 | Sepiplus 400 | 1.25 |
| 8 | Active ingredient | 0 |
| 9 | 2 Na EDTA | 0.2 |

The results observed on the Melanoderm B model are given in Table 2 below:

TABLE 2

Epidermis rating (3 independent observers) vs. negative control (water)

| Formula | | Observations | | | |
|---|---|---|---|---|---|
| | | D 3 | D 7 | D 10 | D 14 |
| Negative control (water) | | | | | |
| 2% kojic acid | 2% aqueous sol. | C (2/3) | C (3/3) | C (2/3) | C (2/3) |
| Simplex control formula | | C (1/3) | C (2/3) | F (1/3) | F (1/3) |
| Example 8 | 0.5% Simplex | C (3/3) | C (3/3) | C (3/3) | C (3/3) |
| Example 21 | 0.5% Simplex | C (2/3) | C (3/3) | C (3/3) | C (2/3) |

Dx: day of dosage or observation
C: epidermis colour lighter (depigmented) vs. absolute control
F: epidermis colour darker (propigmented) vs. absolute control
I: epidermis colour identical vs. absolute control
(X/X): number of observations for the effect observed The coloration of the epidermis is compared to that of the negative control (water). The Simplex control formula does not show any macroscopic depigmenting effect (except on D7): this formula thus does not have any specific effect with respect to the negative control. On the other hand, the formulas containing the compounds according to example 8 or example 21 show a macroscopic depigmenting effect on D3, D7, D10 and D14 on the Melanoderm B (Black) epidermis model. These results indeed show a specific depigmenting effect for formulated examples 8 and 21.

The results observed on the Melanorderm A model are recorded in table 3 below:

TABLE 3

Epidermis rating (3 independent observers) vs. Simplex control formula

| Formula/Vehicle | | Observations | | | |
|---|---|---|---|---|---|
| | | D 6 | D 10 | D 14 | D 21 |
| Example 8 | 0.5% Simplex | C (3/3) | C (3/3) | C (2/3) | C(3/3) |
| Kojic acid | 2% aqueous sol. | C (3/3) | C (3/3) | C (3/3) | C(3/3) |

Dx: day of the dosage or the observation
C: epidermis colour lighter (depigmented) vs. corresponding control
F: epidermis colour darker (propigmented) vs. corresponding control
I: epidermis colour identical vs. corresponding control
(X/X): number of observations for the effect observed The formula containing example 8 was also tested in a Melanoderm-A (Asian) model. The coloration of the epidermis is compared to that of the simplex control formula. The formula containing example 8 shows a macroscopic depigmenting effect on D6, D10, D14, D21. The melanin assay carried out according to the technique described by S. Bessous-Touya (J. Invest. Dermatol. 111: 1103-1109 (1998)), shows a reduction of 4.1 µg of melanin with respect to the epidermises treated by the Simplex control formula.

4) Compositions

The present invention also relates to a pharmaceutical or cosmetic composition, characterised in that it comprises as active ingredient at least one compound of generic formula (I'):

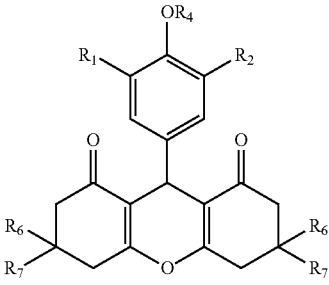

in which the radicals $R_1$, $R_2$, $R_3$, $R_4$, $R_5$, $R_6$ and $R_7$ have identical significations to those given previously, but in which $R_4$ may represent in addition a hydrogen atom or an acetyl radical in association with a pharmaceutically or cosmetically acceptable excipient.

The pharmaceutical or cosmetic composition according to the invention is characterised in that the quantity of compound of generic formula (I') varies between 0.01% and 10% by weight and preferably from 0.1% to 5% by weight with respect to the total weight of the composition.

The pharmaceutical or cosmetic composition comprising a compound of generic formula (I') according to the invention is characterised in that it is intended for the depigmentation of the skin and/or head hair and/or body hair, the treatment and/or the prevention of ageing of the skin or the treatment and/or the prevention of the inflammation of the skin.

The composition according to the invention may moreover comprise conventional cosmetic adjuvants especially chosen from fatty phases, organic solvents, thickeners, softeners, opacifiers, stabilisers, emollients, anti-foaming agents, hydrating agents, fragrances, humectants, gelling agents, preservatives such as parabenes, polymers, fillers, sequestering agents, bactericides, odour absorbents, alkalising or acidifying agents, surfactants, pH adjusters, anti-free radicals, anti-oxidants, vitamins E and C, α-hydroxyacids, or thermal water such as Avène thermal water or any other ingredient normally used in cosmetics, in particular for the production of compositions of this type.

The composition according to the invention may moreover comprise a fatty phase. The fatty phase may be constituted of an oil or a wax or mixtures thereof, and also comprise fatty acids, fatty alcohols, and fatty acid esters. The oils may be chosen from animal, plant, mineral or synthetic oils and especially among vaseline oil, paraffin oil, silicone oils, volatile or not such as dimethicone; isoparaffins, polyolefins, fluorinated and perfluorinated oils. Similarly, the waxes may be chosen from animal, fossil, plant or synthetic waxes such as bee waxes, candelilla waxes, canauba waxes, karite butter, petroleum wax (or microcrystalline wax), paraffin, and mixtures thereof.

The composition according to the invention may moreover comprise a polyol miscible in water at ambient temperature (around 25° C.), especially chosen from polyols having particularly from 2 to 20 carbon atoms, preferably having from 2 to 10 carbon atoms, and preferentially having from 2 to 6 carbon atoms, such as glycerine; derivatives of glycol such as propylene glycol, butylene glycol, pentylene glycol, hexylene glycol, dipropylene glycol, diethylene glycol; glycol ethers such as $C_1$-$C_4$ alkyl ethers of mono-, di- or tri-propylene glycol, $C_1$-$C_4$ alkyl ethers of mono-, di- or tri-ethylene glycol; and mixtures thereof.

The composition according to the invention may also comprise thickening agents or rheology modification agents, such as for example non ionic ethoxylated hydrophobically modified urethanes, polycarboxylic acid thickeners such as copolymers of acrylates/steareth-20 methacrylate, carbomers, acrylate copolymers and mixtures thereof.

The composition according to the invention may also comprise acids and bases making it possible to adjust the pH range of said composition. The bases may be inorganic (sodium hydroxide, potassium hydroxide, aqueous ammonia, etc.) or organic such as mono-, di- or tri-ethanolamine, aminomethylpropanediol, N-methyl-glucamine, basic amino acids such as arginine and lysine, and mixtures thereof.

The composition according to the invention may also comprise skin conditioning agents. Examples of skin conditioning agents include, but are not limited to, emulsifying agents, anionic, cationic and non ionic emulsifiers such as sodium lauryl sulphate, sodium dioctyl sulphosuccinate, sodium stearate, sorbitan ester; ethoxylated fatty acids; ethoxylated fatty alcohols such as trideceth-9 and PEG-5 ethylhexanoate; stearic acid; any other emulsifier and conditioning agent known to those skilled in the art; and mixtures thereof.

The composition according to the invention may moreover contain other active ingredients leading to a complementary effect.

The composition according to the invention may be in any form appropriate for a topical application, particularly on the skin and/or the head hair. In particular, they can be in the form of emulsions obtained by the dispersion of an oily phase in an aqueous phase, for example an oil-in-water or water-in-oil or multiple emulsion, or in the form of a gel, or in the form of an injectable filler, or a liquid, paste or solid anhydrous product, or in the form of a dispersion in the presence of spherules. The composition according to the invention may also be less fluid and be in the form of a white or coloured cream, an ointment, a milk, a lotion, a serum, a paste, a mask, a powder, a solid stick, or, if appropriate, an aerosol, a foam or a spray.

Example of Composition:

| Ingredients (trade names) | INCI designation | Percentage by weight | Function |
| --- | --- | --- | --- |
| I. Purified water | Water | QS 100% | |
| Hydrolite 5 | Pentylene Glycol | 3 | Humectant, Preservative |
| EDTA, 2Na | Disodium EDTA | 0.1 | Complexing agent |
| Microcare PM4 | Phenoxyethanol-Parabene | 0.8 | Preservatives |
| PCL Hydrosoluble | Trideceth-9 & PEG-5 Ethylhexanoate | 1.5 | Aqueous emollient |
| II. Pemulen TR-1 | Acrylates/C10-30 Alkyl Crosspolymer | 0.5 | Gelling agent, stabilising agent |
| III. Stearine TP | Stearic acid | 2 | Emulsifier, consistency factor |
| Liquid PCL | Cetearylethylhexanoate & Isopropylmyristate | 3 | Emollient |
| DC200 | Dimethicone | 0.3 | Emollient |
| Myritol 318 | Capric or caprylic triglycerides | 3 | Emollient |
| Primol 352 | Liquid paraffin | 2 | Emollient |
| IV. Depigmenting active ingredient: Compound of generic formula (I') | | | Active ingredient |
| V. Sodium hydroxide | NaOH | 0.08 | pH adjuster |

In such a composition, the percentage of active ingredient can vary between 0.01% and 10% by weight and preferably from 0.1% to 5% by weight with respect to the total weight of the composition.

The invention claimed is:
1. Compound of generic formula (I):

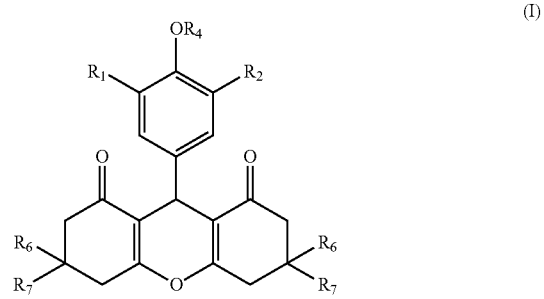

in which:
$R_1$ and $R_2$ represent simultaneously or independently: OH, a hydrogen atom, a $C_1$-$C_6$ alkyl radical, a $C_1$-$C_6$ alkoxy radical, a halogen, or $OCOR_3$;
$R_3$ represents: a $C_1$-$C_{24}$ alkyl radical, a $C_{12}$-$C_{24}$ alkenyl radical comprising at least one unsaturation;
$R_4$ represents: $COR_5$ or a pyranose radical which may be partially or totally acetylated;
$R_5$ represents: a $C_{10}$-$C_{24}$ alkyl radical, or a $C_{12}$-$C_{24}$ alkenyl radical comprising at least one unsaturation;
$R_6$ and $R_7$ represent:
simultaneously a hydrogen atom or a methyl radical, or
when $R_6$ represents a hydrogen atom, $R_7$ represents a $C_1$-$C_6$ alkyl radical or a phenyl substituted or not by one or more $C_1$-$C_3$ alkoxy radical(s) or one or more halogen(s) or
$R_6$ and $R_7$ are bonded to each other and form a $C_3$-$C_6$ cycloalkyl, and pharmaceutically or cosmetically acceptable salts.

2. Compound of generic formula (I) according to claim 1, characterised in that $R_1$ and $R_2$ represent simultaneously or independently a hydrogen atom or a $C_1$-$C_6$ alkoxy radical.

3. Compound of generic formula (I) according to claim 1, characterised in that $R_4$ represents $COR_5$.

4. Compound of generic formula (I) according to claim 1, characterised in that $R_5$ represents a $C_{14}$-$C_{18}$ alkyl radical or a $C_{14}$-$C_{18}$ alkenyl radical comprising from 1 to 3 unsaturations.

5. Compound of generic formula (I) according to claim 1, characterised in that $R_4$ represents a pyranose radical, which may be partially or totally acetylated.

6. Compound of generic formula (I) according to claim 1, characterised in that $R_6$ and $R_7$ represent simultaneously a methyl radical.

7. Compound of generic formula (I) according to claim 1, characterised in that it is chosen from one of the following compounds:
- -2-methoxy-4-(3,3,6,6-tetramethyl-1,8-dioxo-2,3,4,5,6,7,8,9-octahydro-1H-xanthen-9-yl)phenyl palmitate
- -(9Z,12Z)-2-methoxy-4-(3,3,6,6-tetramethyl-1,8,-dioxo-2,3,4,5,6,7,8,9-octahydro-1H-xanthen-9-yl)phenyl octadeca-9,12-dienoate
- -(3R,4S,5S)-2-(acetoxymethyl)-6-(2-methoxy-4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate
- -9-(3-methoxy-4-((3S,4S,5S)-3,4,5-trihydroxy-6-(hydroxymethyl)tetrahydro-2H-pyran-2-yloxy)phenyl)-3,3,6,6-tetramethyl-3,4,5,6,7,9-hexahydro-1H-xanthene-1,8(2H)-dione
- -(3S,4S,5S,6S)-2-(acetoxymethyl)-6-(2-methoxy-4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate
- -9-(3-methoxy-4-((2S,3S,4S,5R)-3,4,5-trihydroxy-6-(hydroxymethyl)tarahydro-2H-pyran-2-yloxy)phenyl)-3,3,6,6-tetramethyl-3,4,5,6,7,9-hexahydro-1H-xanthene-1,8(2H)-dione
- -(3R,4S,5S,6S)-2-(acetoxymethyl)-6-(4-(3,3,6,6-tetramethyl-1,8-dioxo-2,3,4,5,6,7,8,9-octahydro-1H-xanthen-9-yl)phenoxy)tetrahydro-2H-pyran-3,4,5-triyl triacetate
- -3,3,6,6-tetramethyl-9-(4-((2S,3S,4S,5S)-3,4,5-trihydroxy-6-(hydroxymethyl)tetrahydro-2H -pyran-2-yloxy)phenyl)-3,4,5,6,7,9-hexahydro-1H-xanthene- 1,8 (2H)-dione.

8. Compound of generic formula (I'):

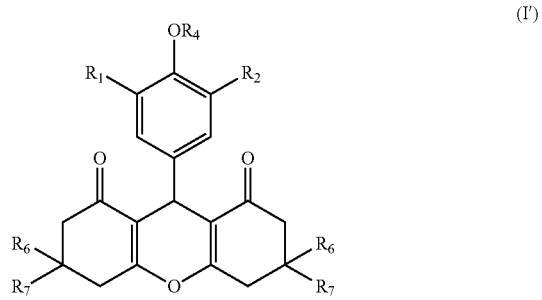

(I')

in which the radicals $R_1$, $R_2$, $R_3$, $R_4$, $R_5$, $R_6$ and $R_7$ have identical significations to those given in claim 1, but in which $R_4$ may in addition represent a hydrogen atom or an acetylated radical, and cosmetically or pharmaceutically acceptable salts, for its use as medicine or as cosmetic active ingredient.

9. Compound of generic formula (I') according to claim 8, characterised in that $R_4$ represents a hydrogen atom for its use as medicine or as cosmetic active ingredient.

10. A method of depigmenting skin and/or head hair and/or body hair, in the treatment of ageing of skin or in the treatment of skin inflammation, which comprises administering to a patient in need thereof an effective amount of a compound of formula (I') according to claim 8.

11. Pharmaceutical or cosmetic composition, characterised in that it comprises as active ingredient at least one compound of generic formula (I') as defined according to claim 8 in association with a pharmaceutically or cosmetically acceptable excipient.

12. Pharmaceutical or cosmetic composition according to claim 11, characterised in that the quantity of compound of formula (I') varies between 0.01% and 10% by weight with respect to the total weight of the composition.

13. A method of depigmenting skin and/or head hair and/or body hair, in the treatment of ageing of skin or in the treatment of skin inflammation, which comprises administering to a patient in need thereof an effective amount of a composition according to claim 11.

14. Method for synthesising compounds of generic formula (I) according to claim 1, characterised in that two molecules of 1,3-diketone are made to react with an aldehyde in the presence of an acid or basic catalyst:

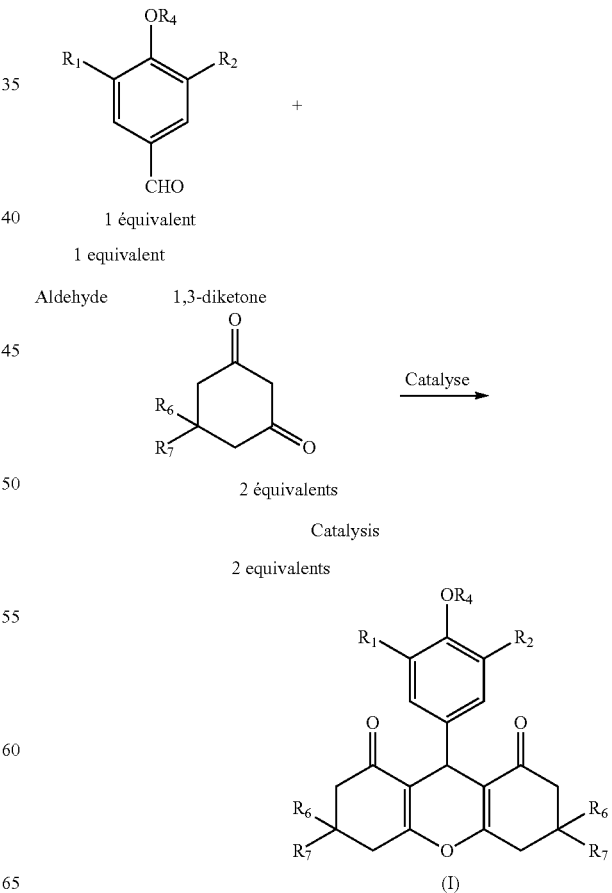

with $R_1$, $R_2$, $R_3$, $R_4$, $R_5$, $R_6$ and $R_7$ having the same significations as in claim 1.

15. Method for synthesising compounds of generic formula (I) according to claim 1, characterised in that a phenol is made to react with a $R_5COCl$ activated carboxylic acid in the presence of a base:

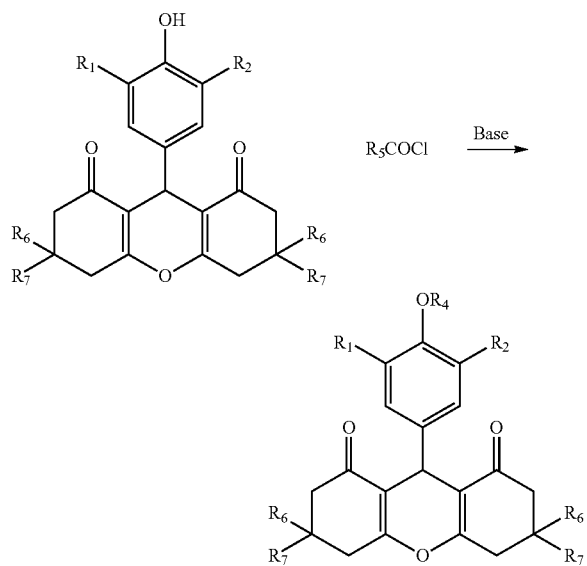

with $R_1$, $R_2$, $R_3$, $R_5$, $R_6$ and $R_7$ having the same significations as in claim 1 and $R_4$ represents $COR_5$.

16. Method for synthesising compounds of generic formula (I) according to claim 1, characterised in that a phenol is made to react with a glucide radical substituted by one or more acetyl radical(s) in the presence of a Lewis acid, $BF_3$, $Et_2O$:

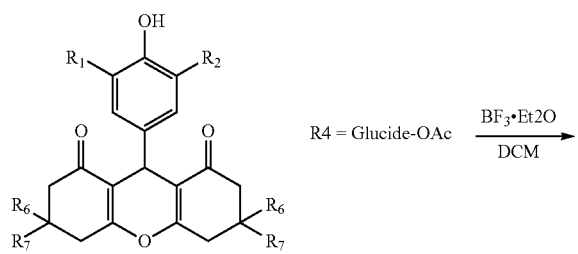

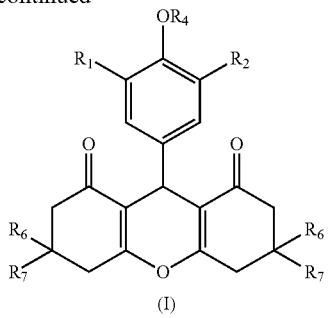

(I)

with $R_1$, $R_2$, $R_3$, $R_5$, $R_6$ and $R_7$ having the same significations as in claim 1, and $R_4$ represents a glucide radical substituted by one or more acetyl radical(s), which may be followed by a saponification step.

17. Compound of generic formula (I) according to claim 2, characterised in that $R_4$ represents $COR_5$.

18. Compound of generic formula (I) according to claim 2, characterised in that $R_5$ represents a $C_{14}$-$C_{18}$ alkyl radical or a $C_{14}$-$C_{18}$ alkenyl radical comprising from 1 to 3 unsaturations.

19. Compound of generic formula (I) according to claim 3, characterised in that $R_5$ represents a $C_{14}$-$C_{18}$ alkyl radical or a $C_{14}$-$C_{18}$ alkenyl radical comprising from 1 to 3 unsaturations.

20. Compound of generic formula (I) according to claim 2, characterised in that $R_4$ represents a pyranose radical, which may be partially or totally acetylated.

21. The compound according to claim 1, wherein $R_3$ represents a $C_{12}$-$C_{24}$ alkenyl radical comprising from 1 to 6 unsaturations.

22. The compound according to claim 1, wherein $R_3$ represents a $C_{12}$-$C_{24}$ alkenyl radical comprising from 1 to 4 unsaturations.

23. The compound according to claim 1, wherein $R_5$ represents a $C_{12}$-$C_{24}$ alkenyl radical comprising from 1 to 6 unsaturations.

24. The compound according to claim 1, wherein $R_5$ represents a $C_{12}$-$C_{24}$ alkenyl radical comprising from 1 to 4 unsaturations.

25. The pharmaceutical or cosmetic composition according to claim 11, characterised in that the quantity of compound of formula (I') varies between 0.1% to 5% by weight with respect to the total weight of the composition.

* * * * *